(12) United States Patent
Ibrahim

(10) Patent No.: US 7,225,026 B2
(45) Date of Patent: May 29, 2007

(54) MONITOR FOR AUDITORY PROSTHESIS

(75) Inventor: Ibrahim Hanna Ibrahim, North Ryde (AU)

(73) Assignee: Cochlear Limited, New South Wales (AU)

( * ) Notice: Subject to any disclaimer, the term of this patent is extended or adjusted under 35 U.S.C. 154(b) by 490 days.

(21) Appl. No.: 10/250,635

(22) PCT Filed: Jun. 5, 2002

(86) PCT No.: PCT/AU02/00726

§ 371 (c)(1),
(2), (4) Date: Jul. 3, 2003

(87) PCT Pub. No.: WO02/098503

PCT Pub. Date: Dec. 12, 2002

(65) Prior Publication Data

US 2004/0049242 A1    Mar. 11, 2004

(30) Foreign Application Priority Data

Jun. 6, 2001    (AU) ..................... PR5513

(51) Int. Cl.
*A61N 1/20* (2006.01)
*A61N 1/08* (2006.01)

(52) U.S. Cl. ................. 607/56; 607/55; 607/57; 623/10

(58) Field of Classification Search ............ 607/55–57; 623/10
See application file for complete search history.

(56) References Cited

U.S. PATENT DOCUMENTS

| | | | |
|---|---|---|---|
| 4,532,930 A * | 8/1985 | Crosby et al. | 607/57 |
| 5,584,869 A * | 12/1996 | Heck et al. | 607/57 |
| 5,824,022 A * | 10/1998 | Zilberman et al. | 607/57 |
| 5,941,905 A | 8/1999 | Single | |
| 6,195,585 B1 | 2/2001 | Karunasiri et al. | |
| 6,212,431 B1 | 4/2001 | Hahn et al. | |

OTHER PUBLICATIONS

International Search Report of PCT/AU02/00726, dated Jul. 9, 2002.
International Preliminary Examination Report of PCT/AU02/00726, dated Nov. 15, 2002.
Written Opinion of PCT/AU02/00726, dated Aug. 12, 2002.

* cited by examiner

*Primary Examiner*—Robert E. Pezzuto
*Assistant Examiner*—Tammie K. Heller
(74) *Attorney, Agent, or Firm*—Christie, Parker & Hale, LLP

(57) ABSTRACT

An auditory prosthesis includes an implanted component and an external component. The external component includes a transmitter for transmitting electromagnetic signals to the implanted component; means for detecting electromagnetic emissions of the transmitter; and means for indicating when the electromagnetic emissions of the transmitter have been detected.

28 Claims, 2 Drawing Sheets

MONITOR FOR AUDITORY PROSTHESIS

CROSS-REFERENCE TO RELATED APPLICATION

This application is a National Phase Patent Application of International Application Number PCT/AU02/00726, filed on Jun. 5, 2002, which claims priority of Australian Patent Application Number PR 5513, filed Jun. 6, 2001.

TECHNICAL FIELD

The present invention relates to a method and apparatus for monitoring the operation of an auditory prosthesis, and in particular for monitoring the operation of a transmitter of an auditory prosthesis.

BACKGROUND ART

Cochlear implant systems have been developed in order to deliver electrical stimulation directly to the auditory nerve. Such a stimulation bypasses hair cells of the cochlea, which may be damaged or missing in persons who are profoundly deaf, and allows the brain to perceive a sensation resembling the natural hearing sensation normally delivered to the auditory nerve. U.S. Pat. No. 4,532,930, the contents of which are incorporated herein by reference, provides a description of one type of cochlear implant system.

Cochlear implant systems typically comprise two components, firstly an external component commonly referred to as a processor unit, and secondly an implanted component commonly referred to as a stimulator/receiver unit. The external processor unit typically has a microphone for detecting sound, a speech processor for converting the detected sounds into a coded signal, a power source such as a battery, and an external transmitter coil for transmitting the coded signal to the implanted stimulator/receiver unit. The implanted stimulator/receiver unit usually includes a receiver coil for receiving the coded signal from the external transmitter coil, and a stimulator for processing the coded signal and for controlling stimuli applied by an intracochlea electrode assembly.

When a malfunction arises during operation of such systems, it is desirable to provide a non-subjective indication of that malfunction. For instance, where the system is used on a person who has been profoundly deaf since birth, the implant recipient is often unable to provide an accurate indication of whether the implant is operating correctly. Further, where the implant recipient is an infant, the infant is unable to provide any subjective indication of unsatisfactory or faulty operation. Previous systems have monitored battery strength in the external processor unit, however such monitors fail to indicate malfunctions which may arise in the microphone, speech processor, transmitter coil, or implanted stimulator/receiver unit.

A further solution, set out in U.S. Pat. No. 5,941,905, has been to provide a guardian/teacher with a "wand", comprising an antenna to detect emissions of a recipient's implant, However this arrangement necessitates individually checking each and every implant, which can be a particularly time consuming process where multiple implant recipients are present, and further complicates the already demanding task of teaching or nursing infants. Further, with recent efforts to minimise electromagnetic interference caused by the RF link of such an implant, the performance of such "wands" may become less reliable, as minimal leakage fields may exist for the wand to detect.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, the present invention resides in an external portion of an auditory prosthesis, the external portion comprising:

a transmitter for transmitting electromagnetic signals to an implanted receiver;

means for detecting electromagnetic emissions of the transmitter; and means for indicating when electromagnetic emissions of the transmitter have been detected.

According to a second aspect, the present invention resides in an auditory prosthesis comprising an implanted component and an external component, the external component comprising:

a transmitter for transmitting electromagnetic signals to the implanted component;

means for detecting electromagnetic emissions of the transmitter; and means for indicating when electromagnetic emissions of the transmitter have been detected.

By providing means for detecting electromagnetic emissions of the transmitter, and means for indicating when such emissions have been detected, the present invention provides an indication of whether the transmitter itself is operating properly, but also an indication of whether all upstream components are operating properly. Further, where the means for indicating comprises a light emitting diode (LED) or the like, the present invention provides a convenient indication of proper operation of the external processor unit, which can significantly ease a task such as verifying proper operation of each auditory prosthesis of a large number of recipients, such as a class of school children.

Preferably, the means for indicating provides a positive indication of when electromagnetic emissions have been detected from the transmitter. For example, detection of such emissions may be positively indicated by switching a LED ON whenever such emissions are indicated. Such positive indication is advantageous in that a supervisor, teacher, carer, nurse, or the like will know that while the positive indication exists, for example while the LED is ON, the transmitter is functioning. Should the positive indication cease, for example should the LED turn OFF, it will be known that a fault has occurred. Such an arrangement provides for detection of faults in the external component of the prosthesis, such as a fault in a microphone, power source, processor, cables or the transmitter itself. Further, such positive indication also provides for detection of faults in the monitoring means or indicating means, as such a fault will also cause the positive indication to cease, for example causing a LED to turn OFF, and thus providing a visual indication of any such fault to a supervisor.

The means for indicating may alternatively provide a negative indication of when electromagnetic emissions have been detected, for example by keeping an LED OFF while electromagnetic emissions are detected, and only turning the LED ON when electromagnetic emissions are not detected. However, in such arrangements, should a fault occur in the monitoring means or the indicating means, a cessation of electromagnetic emissions will not lead to the LED being turned on, and thus the cessation of electromagnetic emission will not be indicated to a supervisor.

The auditory prosthesis will typically be a cochlear implant system, while the transmitter will typically be a transmitter coil, comprising one or more turns.

The means for detecting electromagnetic emissions of the transmitter preferably comprises a shield placed in close proximity to the transmitter, wherein a voltage of the shield induced by electromagnetic emissions of the transmitter coil causes the means for indicating to indicate that electromagnetic emissions of the transmitter have been detected. The use of a shield as the means for detecting is advantageous as, typically, minimal power is drawn by such a shield, which is important in considering the lifetime of a power source of an auditory prosthesis, such as a battery. The shield could comprise one or more open-circuit turns of substantially identical dimensions to turns of the transmitter coil. The voltage of the shield may be taken from one or more such open-circuit turns. Further, the shield is preferably adapted to minimise electromagnetic interference (EMI) caused by the transmitter. Similarly, the shield is preferably positioned relative to the transmitter so as to minimise EMI. Such shielding of EMI is advantageous as devices causing excessive EMI are often not permitted in EMI-sensitive environments, for example medical centres. This can be particularly inconvenient for an unshielded implant recipient who may be required to turn their implant off before entering. Given that implant recipients must often enter such environments due to the medical or clinical requirements associated with the implant, minimising EMI may be of significant advantage to the implant recipient.

Further, the means for detecting and the means for indicating may be implemented by a relatively simple circuit. For instance, electrical DC power rails for the means for detecting and/or the means for indicating may be implemented by rectifying a signal to be transmitted by the transmitter coil, and filtering the rectified signal to produce a relatively constant DC power source. Further, the voltage of the shield induced by electromagnetic emissions of the transmitter coil may be passed to the gate or base of a transistor controlling operation of the indicating means. As transistors typically require only very small signals at their gate or base, such embodiments of the invention will cause very little power to be drawn from the shield, and so the shield will have minimal or negligible impact on the electromagnetic emissions of the transmitter coil. Preferably, a LED and transistor are connected in series across the DC power rails, and the transistor is turned ON when a voltage is induced in the means for detecting electromagnetic emissions of the transmitter coil. When the transistor is turned ON, current is allowed to flow through the LED, causing the LED to emit light and thereby indicate that electromagnetic emissions have been detected from the transmitter coil.

Further, due to the possibility of the transmitter coil transmitting signals of differing frequency, the voltage induced in the shield by the electromagnetic emissions of the transmitter coil is preferably rectified and low-pass filtered to prevent the transistor from changing state at the frequency of the transmitted signal, which may lead to variable brightness of the LED. Further, a relatively high resistance is preferably placed in series with the shield in order to maintain relatively high impedance and thereby minimise: (a) loading on the transmitter coil; (b) alteration of the quality factor of the transmitter coil; and (c) alteration of the electromagnetic field transmitted by the transmitter coil.

According to a third aspect the present invention resides in a method of monitoring operation of an auditory prosthesis, comprising the steps of:

providing an external portion of the auditory prosthesis with indicating means for indicating whether electromagnetic emissions have been detected;

detecting electromagnetic emissions of a transmitter; and actuating said indicating means based on whether electromagnetic emissions of the transmitter have been detected.

Preferably, said step of actuating comprises positively actuating the indicating means when electromagnetic emissions are detected, and negatively actuating the indicating means when electromagnetic emissions are not detected.

In some embodiments of the method of the third aspect of the invention, the step of detecting may comprise placing a shield proximal to the transmitter, and monitoring a voltage of the shield induced by electromagnetic emissions of the transmitter. In such embodiments, the step of indicating may comprise passing the voltage of the shield to a transistor, such that the transistor is turned on when a voltage is induced in the shield. Preferably, such embodiments further comprise the steps of rectifying and low-pass filtering the voltage induced on the shield, in order to prevent the transistor changing state at the frequency of the signal transmitted by the transmitter.

The method of the present invention may further comprise the step of deriving electrical power from a signal to be transmitted by the transmitter. The step of deriving electrical power may comprise rectifying and low pass filtering the signal to be transmitted by the transmitter.

BRIEF DESCRIPTION OF THE DRAWINGS

By way of example only, a preferred embodiment of the invention is described with reference to the accompanying drawings, in which.

DESCRIPTION OF THE INVENTION

Figure 1:
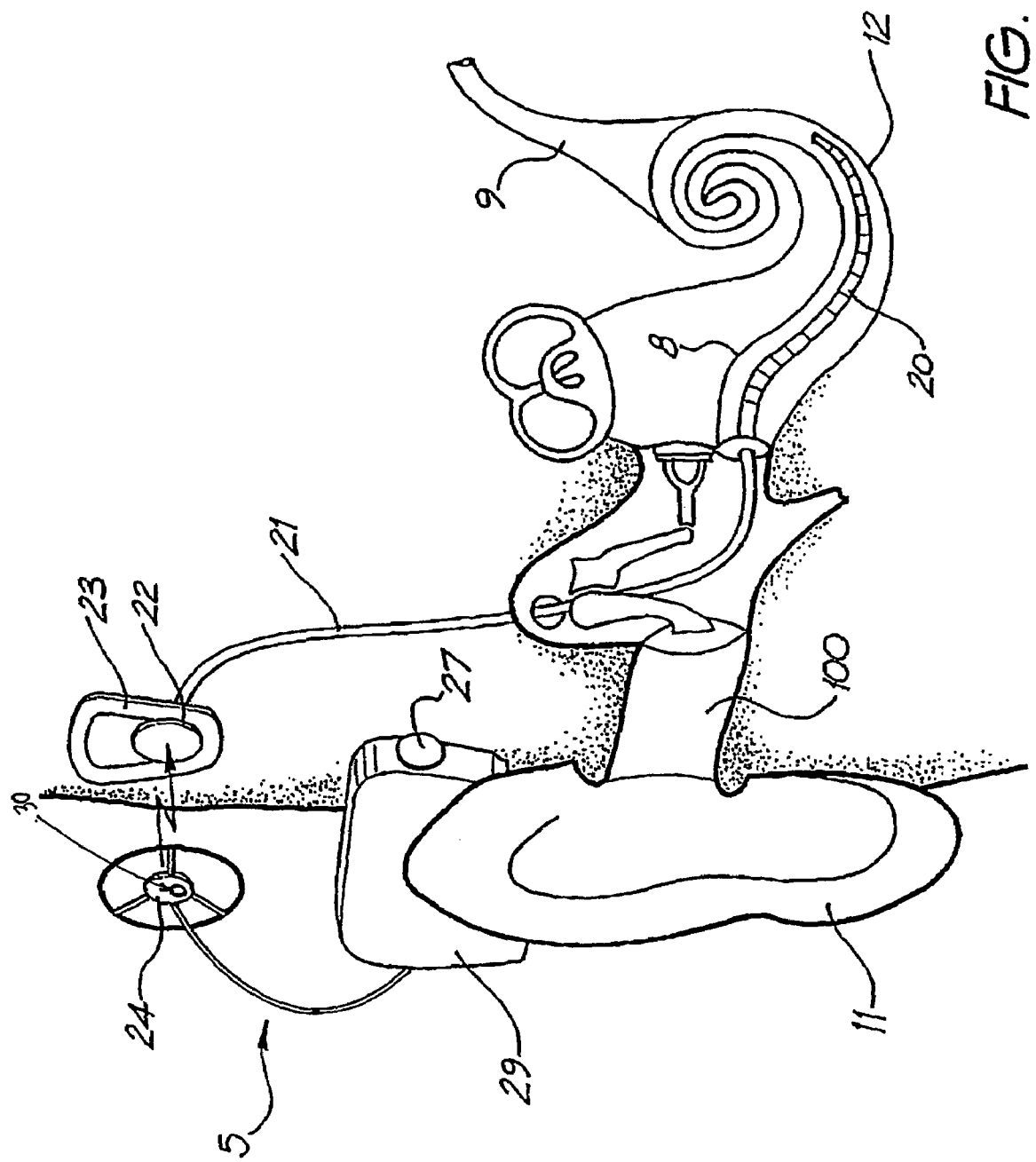
FIG. 1 is a pictorial representation of a cochlear implant system within which the present invention may be implemented.

While the present invention is not directed solely to a cochlear implant, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 that transmits electrical signals to the implanted unit 22 via a radio frequency (RF) link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

As depicted diagrammatically in FIG. 1, the cochlear implant electrode array 20 has traditionally been inserted into the initial portion of the scala tympani of the cochlea 12 up to about a full turn within the cochlea.

The auditory prosthesis 30 comprises a microphone 27 which receives sound and outputs input signals corresponding to the received sound and an output device that provides audio signals in a form receivable by a user of the prosthesis 30. As can be seen, the output device can comprise an earphone (not shown in the diagram) in the case where the prosthesis 30 is a hearing aid. Where the prosthesis 30 is a cochlear implant, the output device comprises an encoder/transmitter unit 32 that outputs encoded data signals to the external transmitter coil 24.

The prosthesis 30 further has a sound processing unit 33 that is operable to receive the input signal provided by the microphone 27 and produce an output signal in a form suitable to operate either the earphone 31 or the encoder/transmitter unit 32.

The nature and function of the sound processor 33 will depend on whether the prosthesis 30 is a cochlear implant or a hearing aid. In the case of a hearing aid, the sound processor 30 includes at least an amplifier whereas in the case of cochlear implant the sound processor 33 will include an amplifier and a speech processor that uses a coding strategy to extract speech from the sounds detected by the microphone 27. In the depicted embodiment, the speech processor of the cochlear implant can perform an audio spectral analysis of the acoustic signals and output channel amplitude levels. The sound processor can also sort the outputs in order of magnitude, or flag the spectral maxima as used in the SPEAK strategy developed by Cochlear Ltd. Other coding strategies could be employed.

In accordance with the present invention, the transmitter coil 24 further comprises an LED indicator 30, which is turned ON whenever electromagnetic emissions from the transmitter coil 24 are detected. The LED 30 is positioned on the transmitter so as to be easily visible to a person other than the implant recipient, for example a school teacher or a child carer. Such a supervisor may thus easily verify that the entire external portion of the implant is operating. As soon as the LED 30 turns OFF, the supervisor becomes aware that a fault exists. The manner in which the LED 30 is controlled is described in more detail with reference to FIG. 2. Alternatively, the LED may be positioned on the external component 29.

Figure 2:
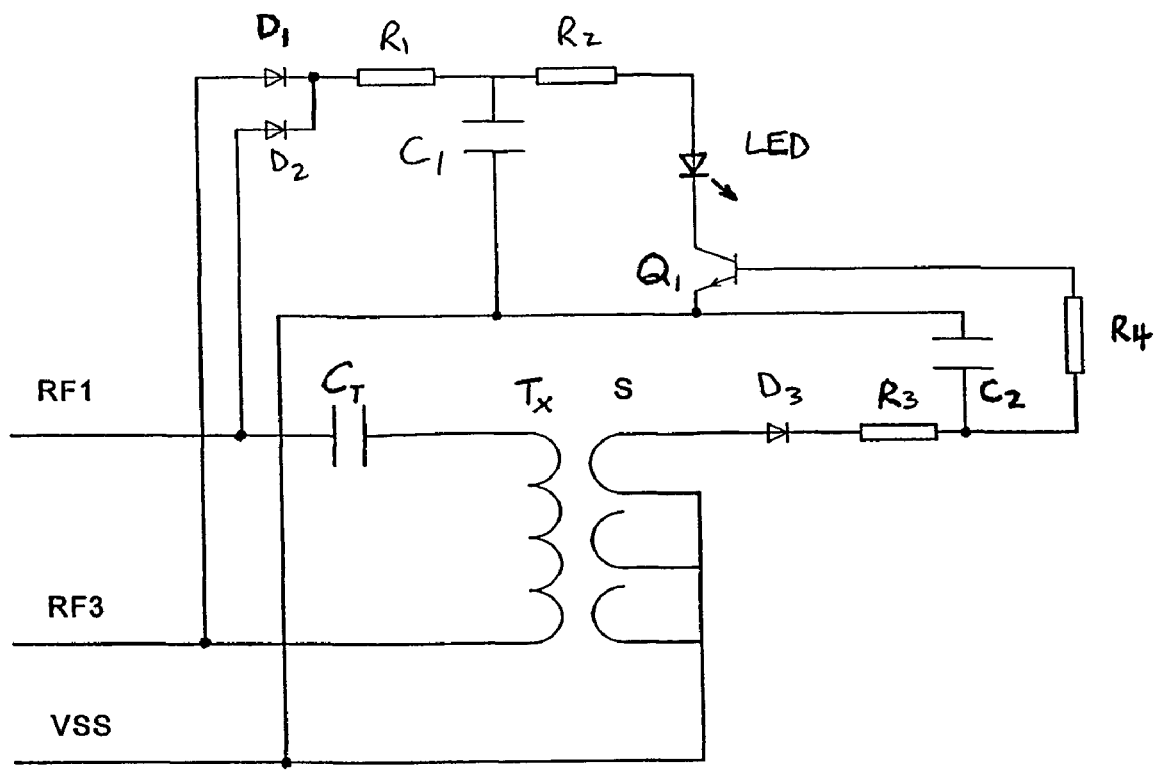
FIG. 2 is a circuit diagram of a monitoring circuit in accordance with the present invention.

FIG. 2 is a circuit diagram illustrating the components of a monitoring circuit in accordance with the present invention. A transmitter $T_x$, consisting of a transmitter coil comprising a number of turns of multi-strand wire, receives a signal to be transmitted from lines RF1 and RF2. The transmitter $T_x$ is designed to be placed against a recipient's skin, and to transcutaneously transmit signals to an implanted component of an auditory prosthesis. Coil $T_x$ is tuned to a desired transmission frequency by tuning capacitor $C_T$.

The monitoring circuit comprises a shield S for detecting electromagnetic emissions of the transmitter $T_x$. The shield S comprises a plurality of open circuit turns of substantially identical dimensions to the turns of the transmitter coil $T_x$, and the shield S is in physical proximity to the transmitter coil $T_x$. At times when the transmitter coil $T_x$ is transmitting signals, a voltage is induced by electromagnetic emissions of the transmitter coil $T_x$. This induced voltage is passed to the base of transistor $Q_1$, causing the transistor $Q_1$ to turn ON and so causing the indicating LED to emit light, thereby positively indicating that electromagnetic emissions of the transmitter $T_x$ have been detected.

The use of a shield S as the means for detecting is advantageous as, typically, minimal power is drawn by such a shield, which is important in considering the lifetime of a power source of the auditory prosthesis, such as a battery. Similarly, the use of $Q_1$ also assists in minimising the load placed on the transmitter coil, due to the very small signals required at the base of transistor $Q_1$.

Prior to being delivered to the base of transistor $Q_1$, the induced voltage of the shield is tailored by $D_3$, $R_3$, $C_2$ and $R_4$. Firstly, diode $D_4$ rectifies the induced voltage of the shield, while capacitor $C_2$ smooths the voltage at the output of the diode. By rectifying and smoothing the induced voltage of the shield, the embodiment shown delivers a tailored control signal to the gate of transistor $Q_1$, avoiding the undesirable circumstance of the transistor $Q_1$ changing state at the frequency of the signal to be transmitted by the transmitter coil $T_x$. Resistor $R_1$ provided in series with shield S, helps to maintain a high impedance of the shield, thereby reducing loading of the transmitter coil, substantially avoiding alteration of the quality factor of the coil, and minimising the effect of the monitor on the transmitted magnetic field. It is further to be noted that by representing proper operation of the transmitter coil by an ON condition of the LED, the embodiment of the monitor of the present invention shown in FIG. 1 provides a positive indication of operation and can also be considered to be 'self diagnosing'. For example, failure of the transistor $Q_1$, LED or power supply components $D_1$, $D_2$, $R_1$, $R_2$ or $C_2$, can cause the LED to remain OFF, thereby indicating improper operation.

By providing means for detecting electromagnetic emissions of the transmitter, and means for indicating when such emissions have been detected, the present invention provides an indication of whether the transmitter $T_x$ itself is operating properly, but also an indication of whether all upstream components are operating properly. Further, the LED of the present embodiment provides a convenient visual indication of proper operation of the transmitter coil $T_x$ and of all upstream components. Such a convenient visual indication can significantly ease a task such as verifying proper operation of each auditory prosthesis of a large number of recipients, such as a school teacher verifying that each child in a class has an operative auditory prosthesis.

In the embodiment of the invention shown in FIG. 1, electrical DC power for the monitor is supplied by rectifying the signal on lines RF1 and RF2, and then filtering the rectified signal to produce a relatively constant DC power source. Diodes $D_1$ and $D_2$ rectify the signal to be transmitted, while $C_1$ and $R_2$ smooth the rectified signal to provide a sufficiently constant power source for the LED and $Q_1$. $R_1$ serves to limit the current drawn by the monitor so as not to overly load the signal source for lines $RF_1$ and $RF_2$.

In circuit conditions such as those present in cochlear implants, such as the cochlear implant disclosed in U.S. Pat. No. 4,532,930, appropriate circuit component values may be as indicated in Table 1.

TABLE 1

| Component | Value |
|---|---|
| $R_1$ | 100 R |
| $C_1$ | 1 uF |
| $R_2$ | 330 R |
| $R_3$ | 1 k |
| $C_2$ | 100 nF |
| $R_4$ | 15 k |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An external portion of an auditory prosthesis comprising:
   a transmitter for transmitting electromagnetic signals to an implanted receiver;
   means for detecting electromagnetic emissions of the transmitter; and
   means for indicating when the electromagnetic emissions of the transmitter have been detected,
   wherein the means for detecting electromagnetic emissions of the transmitter comprises a shield placed in close proximity to the transmitter, whereby a voltage is induced in the shield by electromagnetic emissions of the transmitter coil,
   wherein the transmitter is a transmitter coil comprising one or more turns, and wherein the shield comprises one or more open-circuit turns of substantially identical dimensions to turns of the transmitter coil.

2. The external portion of an auditory prosthesis as claimed in claim 1 wherein the auditory prosthesis is a cochlear implant system.

3. The external portion of an auditory prosthesis as claimed in claim 1 wherein said means for indicating provides a positive indication of detection of electromagnetic emissions.

4. The external portion of an auditory prosthesis as claimed in claim 1 wherein the voltage of the shield induced by electromagnetic emissions of the transmitter coil causes the means for indicating to indicate that electromagnetic emissions of the transmitter have been detected.

5. The external portion of an auditory prosthesis as claimed in claim 1 wherein the voltage of the shield is taken from one or more of the open-circuit turns of the shield.

6. The external portion of an auditory prosthesis as claimed in claim 1 wherein the voltage of the shield induced by electromagnetic emissions of the transmitter coil is passed to the gate or base of a transistor for controlling operation of the indicating means.

7. The external portion of an auditory prosthesis as claimed in claim 1 wherein the shield is adapted to minimize electromagnetic interference caused by the transmitter.

8. The external portion of an auditory prosthesis as claimed in claim 1 wherein the shield is positioned relative to the transmitter so as to minimize electromagnetic interference.

9. An external portion of an auditory prosthesis comprising:
   a transmitter for transmitting electromagnetic signals to an implanted receiver;
   means for detecting electromagnetic emissions of the transmitter; and
   means for indicating when the electromagnetic emissions of the transmitter have been detected,
   wherein electrical DC power rails for the means for detecting and/or for the means for indicating are implemented by rectifying a signal to be transmitted by the transmitter coil, and filtering the rectified signal to produce a substantially constant DC power source.

10. The external portion of an auditory prosthesis as claimed in claim 9 further comprising a LED and a switch connected in series across the DC power rails, wherein the switch is turned ON when a voltage is induced in the means for detecting electromagnetic emissions of the transmitter coil.

11. An external portion of an auditory prosthesis comprising:
    a transmitter for transmitting electromagnetic signals to an implanted receiver;
    means for detecting electromagnetic emissions of the transmitter; and
    means for indicating when the electromagnetic emissions of the transmitter have been detected
    wherein the means for detecting electromagnetic emissions of the transmitter comprises a shield placed in close proximity to the transmitter, whereby a voltage is induced in the shield by electromagnetic emissions of the transmitter coil,
    and wherein the voltage induced in the shield by the electromagnetic emissions of the transmitter coil is rectified and low-pass filtered.

12. An external portion of an auditory prosthesis comprising:
    a transmitter for transmitting electromagnetic signals to an implanted receiver;
    means for detecting electromagnetic emissions of the transmitter; and
    means for indicating when the electromagnetic emissions of the transmitter have been detected,
    wherein a substantially high resistance is placed in series with the means for detecting in order to maintain substantially high impedance.

13. An auditory prosthesis comprising an implanted component and an external component, the external component comprising:
    a transmitter for transmitting electromagnetic signals to the implanted component;
    means for detecting electromagnetic emissions of the transmitter; and
    means for indicating when the electromagnetic emissions of the transmitter have been detected,
    wherein the means for detecting electromagnetic emissions of the transmitter comprises a shield placed in close proximity to the transmitter, whereby a voltage is induced in the shield by electromagnetic emissions of the transmitter coil,
    wherein the transmitter is a transmitter coil comprising one or more turns, and wherein the shield comprises one or more open-circuit turns of substantially identical dimensions to turns of the transmitter coil.

14. The auditory prosthesis as claimed in claim 13 wherein the auditory prosthesis is a cochlear implant system.

15. The auditory prosthesis as claimed in claim 13 wherein said means for indicating provides a positive indication of detection of electromagnetic emissions.

16. The auditory prosthesis as claimed in claim 13 wherein the voltage of the shield induced by electromagnetic emissions of the transmitter coil causes the means for indicating to indicate that electromagnetic emissions of the transmitter have been detected.

17. The auditory prosthesis as claimed in claim 16 wherein the voltage of the shield induced by electromagnetic emissions of the transmitter coil is passed to the gate or base of a transistor for controlling operation of the indicating means.

18. The auditory prosthesis as claimed in claim 13 wherein the voltage of the shield is taken from one or more of the open-circuit turns of the shield.

19. The auditory prosthesis as claimed in claim 13 wherein the shield is adapted to minimize electromagnetic interference caused by the transmitter.

20. The auditory prosthesis as claimed in claim 13 wherein the shield is positioned relative to the transmitter so as to minimize electromagnetic interference.

21. An auditory prosthesis comprising an implanted component and an external component, the external component comprising:
   a transmitter for transmitting electromagnetic signals to the implanted component;
   means for detecting electromagnetic emissions of the transmitter; and
   means for indicating when the electromagnetic emissions of the transmitter have been detected,
   wherein electrical DC power rails for the means for detecting and/or for the means for indicating are implemented by rectifying a signal to be transmitted by the transmitter coil, and filtering the rectified signal to produce a substantially constant DC power source.

22. The auditory prosthesis as claimed in claim 21 further comprising a LED and a switch connected in series across the DC power rails, and wherein the switch is turned ON when a voltage is induced in the means for detecting electromagnetic emissions of the transmitter coil.

23. An auditory prosthesis comprising an implanted component and an external component, the external component comprising:
   a transmitter for transmitting electromagnetic signals to the implanted component;
   means for detecting electromagnetic emissions of the transmitter; and
   means for indicating when the electromagnetic emissions of the transmitter have been detected,
   wherein the means for detecting electromagnetic emissions of the transmitter comprises a shield placed in close proximity to the transmitter, whereby a voltage is induced in the shield by electromagnetic emissions of the transmitter coil,
   and wherein the voltage induced in the shield by the electromagnetic emissions of the transmitter coil is rectified and low-pass filtered.

24. An auditory prosthesis comprising an implanted component and an external component, the external component comprising:
   a transmitter for transmitting electromagnetic signals to the implanted component;
   means for detecting electromagnetic emissions of the transmitter; and
   means for indicating when the electromagnetic emissions of the transmitter have been detected,
   wherein a substantially high resistance is placed in series with the means for detecting in order to maintain substantially high impedance.

25. A method of monitoring operation of an auditory prosthesis, comprising the steps of:
   providing an external portion of the auditory prosthesis with indicating means for indicating whether electromagnetic emissions have been detected;
   detecting electromagnetic emissions of a transmitter; and
   actuating said indicating means based on whether the electromagnetic emissions of the transmitter have been detected,
   wherein the step of detecting comprises placing a shield proximal to the transmitter, and monitoring a voltage of the shield induced by electromagnetic emissions of the transmitter, and
   wherein the step of indicating comprises passing the voltage of the shield to a transistor, such that the transistor is turned on when a voltage is induced in the shield, and rectifying and low-pass filtering the voltage induced on the shield to prevent the transistor changing state at the frequency of the signal transmitted by the transmitter.

26. The method of claim 25, wherein the step of actuating comprises positively actuating the indicating means when electromagnetic emissions are detected, and negatively actuating the indicating means when electromagnetic emissions are not detected.

27. A method of monitoring operation of an auditory prosthesis, comprising the steps of:
   providing an external portion of the auditory prosthesis with indicating means for indicating whether electromagnetic emissions have been detected;
   detecting electromagnetic emissions of a transmitter;
   actuating said indicating means based on whether the electromagnetic emissions of the transmitter have been detected; and
   deriving electrical power from a signal to be transmitted by the transmitter.

28. The method of claim 27, wherein the step of deriving electrical power comprises rectifying and low pass filtering the signal to be transmitted by the transmitter.

* * * * *

UNITED STATES PATENT AND TRADEMARK OFFICE
CERTIFICATE OF CORRECTION

| | |
|---|---|
| PATENT NO. | : 7,225,026 B2 |
| APPLICATION NO. | : 10/250635 |
| DATED | : May 29, 2007 |
| INVENTOR(S) | : Ibrahim Ibrahim |

It is certified that error appears in the above-identified patent and that said Letters Patent is hereby corrected as shown below:

Col. 5, line 57, "signal to be transmitted from lines RF1 and RF2. The" should read -- signal to be transmitted from lines $RF_1$ and $RF_3$. The --.

Col. 6, line 19, "$R_4$. Firstly, diode $D_4$ rectifies the induced voltage of the" should read -- $R_4$. Firstly, diode $D_3$ rectifies the induced voltage of the --.

Col. 6, line 56, "the signal on lines RF1 and RF2, and then filtering the" should read -- the signal on lines $RF_1$ and $RF_3$, and then filtering the --.

Col. 6, line 63, "overly load the signal source for lines $RF_1$ and $RF_2$." should read -- overly load the signal source for lines $RF_1$ and $RF_3$. --.

Signed and Sealed this

Fifth Day of May, 2009

JOHN DOLL
*Acting Director of the United States Patent and Trademark Office*